US006423804B1

United States Patent
Chang et al.

(10) Patent No.: US 6,423,804 B1
(45) Date of Patent: Jul. 23, 2002

(54) ION-SENSITIVE HARD WATER DISPERSIBLE POLYMERS AND APPLICATIONS THEREFOR

(75) Inventors: Yihua Chang; Pavneet S. Mumick, both of Appleton; Frederick J. Lang, Neenah, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/223,999

(22) Filed: Dec. 31, 1998

(51) Int. Cl.[7] ............................................... C08J 22/10
(52) U.S. Cl. .................... 526/319; 526/303.1; 526/320; 526/329.7
(58) Field of Search ................................. 526/319, 320, 526/303.1, 329.7

(56) References Cited

U.S. PATENT DOCUMENTS

| | | |
|---|---|---|
| 2,265,913 A | 12/1941 | Lilienfeld |
| 2,306,451 A | 12/1942 | Lilienfeld |
| 2,831,852 A | 4/1958 | Savage |
| 3,388,082 A | 6/1968 | Rodgers |
| 3,406,688 A | 10/1968 | Cubitt |
| 3,453,261 A | 7/1969 | Scherff |
| 3,709,876 A | 1/1973 | Glomski |
| 3,800,797 A | 4/1974 | Tunc |
| 3,804,092 A | 4/1974 | Tunc |
| 3,839,319 A | 10/1974 | Greminger |
| 3,897,782 A | 8/1975 | Tunc |
| 3,926,951 A | 12/1975 | Lindenfors et al. |
| 3,939,836 A | 2/1976 | Tunc |
| RE28,957 E | 9/1976 | Drelich et al. |
| 4,005,251 A | 1/1977 | Tunc |
| 4,035,540 A | 7/1977 | Gander |
| 4,051,093 A * | 9/1977 | Wendel et al. |
| 4,073,777 A | 2/1978 | O'Neill et al. |
| 4,084,033 A | 4/1978 | Drelich |
| 4,084,591 A | 4/1978 | Takebe et al. |
| 4,117,187 A | 9/1978 | Adams et al. |
| 4,245,744 A | 1/1981 | Daniels et al. |
| 4,258,849 A | 3/1981 | Miller |
| 4,343,403 A | 8/1982 | Daniels et al. |
| 4,372,447 A | 2/1983 | Miller |
| 4,419,403 A | 12/1983 | Varona |
| 4,443,576 A * | 4/1984 | Bhattacharyya et al. .... 524/522 |
| 4,491,645 A | 1/1985 | Thompson |
| 4,671,888 A * | 6/1987 | Yorke ......................... 252/180 |
| 4,702,947 A | 10/1987 | Pall et al. |
| 4,755,421 A | 7/1988 | Manning et al. |
| 4,855,132 A | 8/1989 | Heller et al. |
| 4,894,118 A | 1/1990 | Edwards et al. |
| 5,104,923 A | 4/1992 | Steinwand et al. |
| 5,300,192 A | 4/1994 | Hansen et al. |
| 5,312,883 A | 5/1994 | Komatsu et al. |
| 5,317,063 A | 5/1994 | Komatsu et al. |
| 5,360,826 A | 11/1994 | Egolf et al. |
| 5,362,565 A * | 11/1994 | Murano et al. .......... 428/402.2 |
| 5,384,189 A | 1/1995 | Kuroda et al. |
| 5,500,281 A | 3/1996 | Srinivasan et al. |
| 5,631,317 A | 5/1997 | Komatsu et al. ............ 524/561 |
| 5,770,528 A | 6/1998 | Mumick et al. |
| 5,952,232 A * | 9/1999 | Rothman ..................... 435/459 |

FOREIGN PATENT DOCUMENTS

| | | |
|---|---|---|
| DE | 1 719 395 | 12/1970 |
| EP | 0 303 528 | 2/1989 |
| EP | 0 601 518 | 6/1994 |
| EP | 0 608 460 | 8/1994 |
| EP | 0 726 068 | 8/1996 |
| EP | 0 807 704 | 11/1997 |
| JP | 08-239428 | 9/1996 |
| WO | 96/12615 | 5/1996 |

OTHER PUBLICATIONS

D 5034–11, "Standard Test Method for Breaking Force and Elongation of Textile Fabrics (Grab Test)," *1994 Annual Book of ASTM Standards*, 7.02 p. 708–9 1994.

Carlsson et al Thermal Gelation of Nonionic Cellulose Ethers and Ionic Surfactants in Water *Colloids and Surfaces* 47 147–165 1990.

Chowdhury et al., Direct Observation of the Gelatin of Rodlike Polymers *Polymeric Materials Science and Engineering* 59 1045–1052 1988.

Nagura et al. Temperature–Viscosity Relationships of Aqueous Solutions of Cellulose Ethers *Kobunshi Ronbunshu* 38(3) 133–137 1980.

Stafford et al. Temperature dependence of the disintegration times of compressed tablets containing hydroxypropylcellulose as binder *J. Pharm. Pharmac* 30 1–5 1977.

JAPIO and Derwent WPI, JP 63–139906 (Lion Corp) Jun. 11, 1988, abstract.

JAPIO and Derwent WPI, JP 03–239709 (Lion Corp) Oct. 25, 1991, abstract.

Derwent WPI, JP 01–306661 (Lion Corp) Dec. 11, 1989, abstract.

Derwent WPI, JP 05–179548 (Lion Corp) Jul. 20, 1993, abstract.

\* cited by examiner

*Primary Examiner*—David W. Wu
*Assistant Examiner*—Tanya Zalukaeva
(74) *Attorney, Agent, or Firm*—Kilpatrick Stockton LLP

(57) ABSTRACT

The present invention is directed to ion-sensitive, hard water dispersible polymers. The present invention is also directed to a method of making ion-sensitive, hard water dispersible polymers and their applicability as binder compositions. The present invention is further directed to fiber-containing fabrics and webs comprising ion-sensitive, hard water dispersible binder compositions and their applicability in water dispersible personal care products.

17 Claims, No Drawings

ION-SENSITIVE HARD WATER DISPERSIBLE POLYMERS AND APPLICATIONS THEREFOR

FIELD OF THE INVENTION

The present invention is directed to ion-sensitive, hard water dispersible polymers. The present invention is also directed to a method of making ion-sensitive, hard water dispersible polymers and their applicability as binder compositions. The present invention is further directed to fiber-containing fabrics and webs comprising ion-sensitive, hard water dispersible binder compositions and their applicability in water dispersible personal care products.

BACKGROUND OF THE INVENTION

For many years the problem of disposability has plagued industries, which provide disposable diapers, wet wipes, incontinent garments and feminine care products. While much headway has been made in addressing this problem, one of the weak links has been the inability to create an economical coherent fibrous web, which will readily dissolve or disintegrate in water, but still have in-use strength. See, for example, U.K. patent disclosure 2,241,373 and U.S. Pat. No. 4,186,233. Without such a product, the ability of the user to dispose of the product by flushing it down the toilet is greatly reduced, if not eliminated. Furthermore, the ability of the product to disintegrate in a landfill is quite limited because a large portion of the product components, which may well be biodegradable or photode gradable, are encapsulated in or bound together by plastic which degrades over a long period of time, if at all. Accordingly, if the plastic disintegrated in the presence of water, the internal components could degrade as a result of the rupture of the plastic encapsulation or binding.

Disposable diapers, feminine care products and adult incontinent care products usually comprise a body side liner which must rapidly pass fluids, such as urine or menses, so that the fluid may be absorbed by an absorbent core of the product. Typically, the body side liner is a coherent fibrous web, which desirably possesses a number of characteristics such as softness and flexibility. The fibrous web of the body side liner material is typically formed by wet or dry (air) laying a generally random plurality of fibers and joining them together to form a coherent web with a binder. Past binders have performed this function well. From an environmental standpoint, it might be stated that the past binders have performed this function too well in that the binders tended not to degrade and thus the liner remained intact, severely hampering any environmental degradation of the disposable product.

Recent binder compositions have been developed which are more environmentally responsible and exhibit better water solubility than past binders. One class of binders includes polymeric materials having inverse solubility in water. These binders are insoluble in warm water, but are soluble in cold water, such as found in a toilet. It is well known that a number of polymers exhibit cloud points or inverse solubility properties in aqueous media. These polymers have been cited in several publications for various applications, including (1) as evaporation retarders (JP 6207162); (2) as temperature sensitive compositions, which are useful as temperature indicators due to a sharp color change associated with a corresponding temperature change (JP 6192527); (3) as heat sensitive materials that are opaque at a specific temperature and become transparent when cooled to below the specific temperature (JP 51003248 and JP 81035703); (4) as wound dressings with good absorbing characteristics and easy removal (JP 6233809); and (5) as materials in flushable personal care products (U.S. Pat. No. 5,509,913, issued to Richard S. Yeo on Apr. 23, 1996 and assigned to Kimberly-Clark Corporation).

Other recent binders of interest include a class of binders, which are ion-sensitive. Several U.S. and European patents assigned to Lion Corporation of Tokyo, Japan, disclose ion-sensitive polymers comprising acrylic acid and alkyl or aryl acrylates. See U.S. Pat. Nos. 5,312,883; 5,317,063; and 5,384,189; as well as, European Patent No. 608460A1. In U.S. Pat. No. 5,312,883, terpolymers are disclosed as suitable binders for flushable nonwoven webs. The disclosed acrylic acid-based terpolymers, which comprise partially neutralized acrylic acid, butyl acrylate and 2-ethylhexyl acrylate, are suitable binders for use in flushable nonwoven webs in some parts of the world. However, because of the presence of a small amount of sodium acrylate in the partially neutralized terpolymer, these binders fail to disperse in water containing more than about 15 ppm $Ca^{2+}$ and/or $Mg^{2+}$. When placed in water containing more than about 15 ppm $Ca^{2+}$ and/or $Mg^{2+}$ ions, nonwoven webs using the above-described binders maintain a tensile strength greater than 30 g/in, which negatively affects the "dispersibility" of the web. The proposed mechanism for the failure is that each calcium ion binds with two carboxylate groups either intramolecularly or intermolecularly. Intramolecular association causes the polymer chain to coil up, which eventually leads to polymer precipitation. Intermolecular association yields crosslinking. Whether intramolecular or intermolecular associations are taking place, the terpolymer is not soluble in water containing more than about 15 ppm $Ca^{2+}$ and/or $Mg^{2+}$. Due to the strong interaction between calcium ions and the carboxylate groups of the terpolymer, dissociation of the complex is highly unlikely because this association is irreversible. Therefore, the above-described polymer that has been exposed to a high $Ca^{2+}$ and/or $Mg^{2+}$ concentration solution for about 8 hours or more will not disperse in water even if the calcium concentration decreases. This limits the application of the polymer as a flushable binder material because most areas across the U.S. have hard water, which contains more than 15 ppm $Ca^{2+}$ and/or $Mg^{2+}$.

Although many patents disclose various ion and temperature sensitive compositions for flushable materials, there exists a need for flushable products possessing softness, three dimensionality, and resiliency; wicking and structural integrity in the presence of body fluids at body temperature; and true fiber dispersion after toilet flushing so that fibers do not become entangled with tree roots or at bends in sewer pipes. Moreover, there is a need in the art for flushable products having water-dispersibility in all areas of the world, including soft and hard water areas. Such a product is needed at a reasonable cost without compromising product safety and environmental concerns, something that past products have failed to do.

SUMMARY OF THE INVENTION

The present invention is directed to ion-sensitive polymers, which have been developed to address the above-described problems associated with currently available, ion-sensitive polymers and other polymers described in literature. The ion-sensitive polymers of the present invention have a "trigger property," such that the polymers are insoluble in high salt solutions, but soluble in low salt solutions, including hard water. Unlike some ion-sensitive polymers, which lose dispersibility in hard water because of ion cross-linking by calcium ions, the polymers of the present invention are relatively insensitive to calcium and/or magnesium ions. Consequently, flushable products containing the polymers of the present invention maintain dispersibility in hard water.

The polymeric materials of the present invention are useful as binders and structural components for air-laid and wet-laid nonwoven fabrics for applications such as body-side liner, fluid distribution material, fluid in-take material (surge) or cover stock in various personal care products. The polymeric materials of the present invention are particularly useful as a binder material for flushable personal care products such as diapers, feminine pads, panty liners, and wet wipes. The flushable products maintain integrity during storage and use, and break apart after disposal in the toilet when the salt concentration falls below a critical level.

The present invention also discloses how to make water-dispersible nonwovens, including coverstock (liner), intake (surge) materials and wet wipes, which are stable in fluids having high ionic content, using the above-described unique polymeric binder compositions. The resultant nonwovens are flushable and water-dispersible due to the tailored ion sensitivity, which is triggered regardless of the hardness of water found in toilets throughout the United States and the world.

DESCRIPTION OF THE PREFERRED EMBODIMENTS

In order to be an effective ion triggerable material suitable for use in flushable personal care products, the material should desirably be (1) functional, i.e., maintain wet strength under controlled conditions and dissolve or disperse rapidly in soft or hard water such as found in a toilets and sinks around the world; (2) safe (not toxic); and (3) economical. The ion-sensitive polymers of the present invention meet the above criteria.

Unlike the Lion polymers and other polymers cited in technical literature, the polymers of the present invention are ion triggerable, as well as, soluble in water having from greater than about 15 ppm $Ca^{2+}$ and/or $Mg^{2+}$ to about 200 ppm $Ca^{2+}$ and/or $Mg^{2+}$. The polymers of the present invention have been formulated to minimize the potentially strong interaction between the anions of the polymers and the cations in the water. This strong interaction can be explained via the hard-soft acid-base theory proposed by R. G. Pearson in the *Journal of the American Chemical Society*, vol. 85, pg. 3533 (1963); or N. S. Isaacs in the textbook, *Physical Organic Chemistry*, published by Longman Scientific and Technical with John Wiley & Sons, Inc., New York (1987). Hard anions and hard cations interact strongly with one another. Soft anions and soft cations also interact strongly with one another. However, soft anions and hard cations, and vice-versa, interact weakly with one another. In the Lion polymers, the carboxylate anion of the sodium acrylate is a hard anion, which interacts strongly with the hard cations, $Ca^{2+}$ and/or $Mg^{2+}$, present in moderately hard and hard water. By replacing the carboxylate anions with a softer anion, such as a sulfonate anion, the interaction between the anions of an ion-triggerable polymer and the hard cations, $Ca^{2+}$ and/or $Mg^{2+}$, present in moderately hard and hard water, is reduced.

The polymers of the present invention are formed from one or more monomers such that the resulting polymer has a "hydrophobic/hydrophilic balance" throughout the polymer chain. As used herein, the term "hydrophobic/hydrophilic balance" refers to a balance of hydrophobic and hydrophilic moieties having a controlled degree of hardness or softness, as discussed above, along the polymer chain, which results in a polymer having a desired trigger property in soft, moderately hard, or hard water. As used herein, the term "soft water" refers to water having a divalent ion content of less than about 10 ppm. As used herein, the term "moderately hard water" refers to water having a divalent ion content of from about 10 to about 50 ppm. As used herein, the term "hard water" refers to water having a divalent ion content of more than about 50 ppm. By controlling the hydrophobic/hydrophilic balance and the composition of the polymer, ion-sensitive polymers having desired in-use binding strength and water-dispersibility in hard water are produced.

The polymers of the present invention may comprise any vinyl monomers capable of free radical polymerization. At least a portion of the resulting polymer comprises one or more monomer units having a hydrophobic moiety thereon and one or more monomer units having a hydrophilic moiety thereon. Suitable monomers, which provide a degree of hydrophobicity to the resulting polymer include, but are not limited to, vinyl esters, such as vinyl acetate; alkyl acrylates; acrylonitrile; methacrylonitrile; and vinyl chloride. Suitable monomers, which provide a degree of hydrophilicity to the resulting polymer include, but are not limited to, acrylamide and methacrylamide based monomers, such as acrylamide, N,N-dimethyl acrylamide, N-ethyl acrylamide, N-isopropyl acrylamide, and hydroxymethyl acrylamide; N-vinylpyrrolidinone; N-vinylforamide; hydroxyalkyl acrylates and hydroxyalkyl methacrylates, such as hydroxyethyl methacrylate and hydroxyethyl acrylate; and monomers containing one or more of the following functional groups: hydroxy, amino, ammonium, sulfonate, ether, carboxylate, carboxylic acid, amide, and sulfoamide groups. Other suitable hydrophilic and hydrophobic monomers include the vinyl monomers disclosed in U.S. Pat. No. 5,317,063, assigned to Lion Corporation, Tokyo, Japan, which is herein incorporated by reference in its entirety.

The amount of hydrophobic monomer used to produce the ion-sensitive polymers of the present invention may vary depending on the desired properties in the resulting polymer. Desirably, the mole percent of hydrophobic monomer in the ion-sensitive polymer is up to about 70 mol %. More desirably, the mole percent of hydrophobic monomer in the ion-sensitive polymer is from about 15 to about 50 mol %. Most desirably, the mole percent of hydrophobic monomer in the ion-sensitive polymer is from about 25 to about 40 mol %.

The ion-sensitive polymers of the present invention may have an average molecular weight, which varies depending on the ultimate use of the polymer. Desirably, the ion-sensitive polymers of the present invention have a weight average molecular weight ranging from about 10,000 to about 5,000,000. More desirably, the ion-sensitive polymers of the present invention have a weight average molecular weight ranging from about 25,000 to about 2,000,000.

The ion-sensitive polymers of the present invention may be prepared according to a variety of polymerization methods, preferably a solution polymerization method. Suitable solvents for the polymerization method include, but are not limited to, lower alcohols such as methanol, ethanol and propanol; a mixed solvent of water and one or more lower alcohols mentioned above; and a mixed solvent of water and one or more lower ketones such as acetone or methyl ethyl ketone.

In the polymerization method, any polymerization initiator may be used. Selection of a particular initiator may depend on a number of factors including, but not limited to, the polymerization temperature, the solvent, and the monomers used. Suitable polymerization initiators for use in the present invention include, but are not limited to, 2,2'-azobisisobutyronitrile, 2,2'-azobis(2-methylbutyronitrile), 2,2'-azobis(2,4-dimethylvaleronitrile), 2,2'-azobis(2-amidinopropane)dihydrochloride, 2,2'-azobis(N,N'-dimethyleneisobutylamidine), potassium persulfate, ammonium persulfate, and aqueous hydrogen peroxide. The amount of polymerization initiator may range from about 0.01 to 5 wt % based on the total weight of monomer present.

The polymerization temperature may vary depending on the polymerization solvent, monomers, and initiator used, but in general, ranges from about 20° C. to about 90° C. Polymerization time generally ranges from about 2 to about 8 hours.

In one embodiment of the present invention, hydrophilic monomers, such as acrylic acid or methacrylic acid, are incorporated into the ion-sensitive polymers of the present invention along with one or more sulfonate-containing monomers. The sulfonate anion of these monomers are softer than carboxylate anion since the negative charge of the sulfonate anion is delocalized over three oxygen atoms and a larger sulfur atom, as oppose to only two oxygen atoms and a smaller carbon atom in the carboxylate anion. These monomers, containing the softer sulfonate anion, are less interactive with multivalent ions present in hard water, particularly $Ca^{2+}$ and $Mg^{2+}$ ions. Suitable sulfonate-containing monomers include, but are not limited to, sodium salt of styrenesulfonic acid (NaSS), 2-acrylamido-2-methyl-1-propanesulfonic acid (AMPS), sodium salt of 2-acrylamido-2-methyl-1-propanesulfonic acid (NaAMPS), vinylsulfonic acid, and sodium salt of vinylsulfonic acid. To maintain the hydrophobic/hydrophilic balance of the ion-sensitive polymer, one or more hydrophobic monomers are added to the polymer.

In a further embodiment of the present invention, ion-sensitive polymers are produced from four monomers: acrylic acid, AMPS, butyl acrylate, and 2-ethylhexyl acrylate. Desirably, the monomers are present in ion-sensitive polymer at the following mole percents: acrylic acid, about 50 to less than 67 mol %; AMPS, greater than 0 to about 10 mol %; butyl acrylate, about 15 to about 28 mol %; and 2-ethylhexyl acrylate, about 7 to about 15 mol %. More desirably, the monomers are present in ion-sensitive polymer at the following mole percents: acrylic acid, about 57 to about 66 mol %; AMPS, about 1 to about 6 mol %; butyl acrylate, about 15 to about 28 mol %; and 2-ethylhexyl acrylate, about 7 to about 13 mol %.

In order to further fine tune the hydrophobic/hydrophilic balance of the ion-sensitive polymers, at least a portion of the acid moieties, if present, along the polymer chain may be neutralized. For example, the above-described ion-sensitive polymer comprising four distinct monomers may be partially or wholly neutralized to convert some or all of the AMPS to NaAMPS. Any inorganic base or organic base may be used as a neutralizing agent to neutralize the acid component of the ion-sensitive polymers. Examples of neutralizing agents include, but are not limited to, inorganic bases such as sodium hydroxide, potassium hydroxide, lithium hydroxide and sodium carbonate, and amines such as monoethanolamine, diethanolamine, diethylaminoethanol, ammonia, trimethylamine, triethylamine, tripropylamine, morpholine. Preferred neutralizing agents include ethanolamines, sodium hydroxide, potassium hydroxide, or a combination thereof.

In a further embodiment of the present invention, the above-described ion-sensitive polymers are used as a binder material for flushable and/or non-flushable products. In order to be effective as a binder material in flushable products throughout the United States, the ion-sensitive polymers of the present invention remain stable and maintain their integrity while dry or in high concentrations of monovalent and/or multivalent ions, but become soluble in water containing up to about 200 ppm $Ca^{2+}$ ions. Desirably, the ion-sensitive polymers of the present invention are insoluble in a salt solution containing at least about 0.3 weight percent of one or more inorganic and/or organic salts containing monovalent and/or multivalent ions. More desirably, the ion-sensitive polymers of the present invention are insoluble in a salt solution containing from about 0.3 wt % to about 5.0 wt % of one or more inorganic and/or organic salts containing monovalent and/or multivalent ions. Even more desirably, the ion-sensitive polymers of the present invention are insoluble in a salt solution containing from about 0.5 wt % to about 3.0 wt % of one or more inorganic and/or organic salts containing monovalent and/or multivalent ions. Suitable monovalent and/or multivalent ions include, but are not limited to, $Na^+$ ions, $K^+$ ions, $Li^+$ ions, $NH_4^+$ ions, $Cl^-$ ions, $Ca^{2+}$ ions, $Mg^{2+}$ ions, $Zn^{2+}$ ions, $CO_3^{2-}$ ions, and a combination thereof.

Based on a recent study conducted by the American Chemical Society, water hardness across the United States varies greatly, with $CaCO_3$ concentration ranging from near zero for soft water to about 500 ppm $CaCO_3$ (about 200 ppm $Ca^{2+}$ ion) for very hard water. To ensure polymer dispersibility across the country, the ion-sensitive polymers of the present invention are desirably soluble in water containing up to about 50 ppm $Ca^{2+}$ and/or $Mg^{2+}$ ions. More desirably, the ion-sensitive polymers of the present invention are soluble in water containing up to about 100 ppm $Ca^{2+}$ and/or $Mg^{2+}$ ions. Even more desirably, the ion-sensitive polymers of the present invention are soluble in water containing up to about 150 ppm $Ca^{2+}$ and/or $Mg^{2+}$ ions. Even more desirably, the ion-sensitive polymers of the present invention are soluble in water containing up to about 200 ppm $Ca^{2+}$ and/or $Mg^{2+}$ ions.

The binder formulations of the present invention may be applied to any fibrous substrate. The binders are particularly suitable for use in water-dispersible products. Suitable fibrous substrates include, but are not limited to, nonwoven and woven fabrics. In many embodiments, particularly personal care products, preferred substrates are nonwoven fabrics. As used herein, the term "nonwoven fabric" refers to a fabric that has a structure of individual fibers or filaments randomly arranged in a mat-like fashion. Nonwoven fabrics can be made from a variety of processes including, but not limited to, air-laid processes, wet-laid processes, hydroentangling processes, staple fiber carding and bonding, and solution spinning.

The binder composition may be applied to the fibrous substrate by any known process of application. Suitable processes for applying the binder material include, but are not limited to, printing, spraying, impregnating or by any other technique. The amount of binder composition may be metered and distributed uniformly within the fibrous substrate or may be non-uniformly distributed within the fibrous substrate. The binder composition may be distributed throughout the entire fibrous substrate or it may be distributed within a multiplicity of small closely spaced areas. In most embodiments, uniform distribution of binder composition is desired.

For ease of application to the fibrous substrate, the binder may be dissolved in water, or in a non-aqueous solvent such as methanol, ethanol, acetone, or the like, with water being the preferred solvent. The amount of binder dissolved in the solvent may vary depending on the polymer used and the fabric application. Desirably, the binder solution contains up to about 25 percent by weight of binder composition solids. More desirably, the binder solution contains from about 10 to 20 percent by weight of binder composition solids. Plasticizers, perfumes, coloring agents, antifoams, bactericides, surface active agents, thickening agents, fillers, tackifiers, detackifiers, and similar additives can be incorporated into the solution of binder components if so desired.

Once the binder composition is applied to the substrate, the substrate is dried by any conventional means. Once dry, the coherent fibrous substrate exhibits improved tensile strength when compared to the tensile strength of the untreated wet-laid or dry-laid substrates, and yet has the ability to rapidly "fall apart", or disintegrate when placed in soft or hard water having a relatively low monovalent and/or multivalent ionic concentration and agitated. For example, the dry tensile strength of the fibrous substrate may be increased by at least 25 percent as compared to the dry tensile strength of the untreated substrate not containing the binder. More particularly, the dry tensile strength of the fibrous substrate may be increase by at least 100 percent as compared to the dry tensile strength of the untreated substrate not containing the binder. Even more particularly, the dry tensile strength of the fibrous substrate may be increased by at least 500 percent as compared to the dry tensile strength of the untreated. substrate not containing the binder.

A desirable feature of the present invention is that the improvement in tensile strength is effected where the amount of binder composition present, "add-on", in the resultant fibrous substrate represents only a small portion, by weight of the entire substrate. The amount of "add-on" can vary for a particular application; however, the optimum amount of "add-on" results in a fibrous substrate which has integrity while in use and also quickly disperses when agitated in water. For example, the binder components typically are from about 5 to about 65 percent, by weight, of the total weight of the substrate. More particularly, the binder components may be from about 10 to about 35 percent, by weight, of the total weight of the substrate. Even more particularly, the binder components may be from about 10 to about 25 percent, by weight, of the total weight of the substrate.

The nonwoven fabrics of the present invention have good in-use tensile strength, as well as, ion triggerability. Desirably, the nonwoven fabrics of the present invention are abrasion resistant and retain significant tensile strength in aqueous solutions containing greater than about 0.5 weight percent NaCl or a mixture of monovalent and multivalent ions, wherein the multivalent ion concentration is greater than about 500 ppm. Yet the nonwoven fabrics are dispersible in soft to moderately hard to hard water. Because of this latter property, nonwoven fabrics of the present invention are well suited for disposable products such as sanitary napkins, diapers, and dry and premoistened wipes, which can be thrown in a flush toilet after use in any part of the world.

The fibers forming the fabrics above can be made from a variety of materials including natural fibers, synthetic fibers, and combinations thereof. The choice of fibers depends upon, for example, the intended end use of the finished fabric and fiber cost. For instance, suitable fibrous substrates may include, but are not limited to, natural fibers such as cotton, linen, jute, hemp, wool, wood pulp, etc. Similarly, regenerated cellulosic fibers such as viscose rayon and cuprammonium rayon, modified cellulosic fibers, such as cellulose acetate, or synthetic fibers such as those derived from polyesters, polyamides, polyacrylics, etc., alone or in combination with one another, may likewise be used. Blends of one or more of the above fibers may also be used if so desired.

The fiber length is important in producing the fabrics of the present invention. In some embodiments such as flushable products, fiber length is of more importance. The minimum length of the fibers depends on the method selected for forming the fibrous substrate. For example, where the fibrous substrate is formed by carding, the length of the fiber should usually be at least about 42 mm in order to insure uniformity. Where the fibrous substrate is formed by air-laid or wet-laid processes, the fiber length may desirably be about 0.2 to 6 mm. Although fibers having a length of greater than 50 mm are within the scope of the present invention, it has been determined that when a substantial quantity of fibers having a length greater than about 15 mm is placed in a flushable fabric, though the fibers will disperse and separate in water, their length tends to form "ropes" of fibers which are undesirable when flushing in home toilets. Therefore, for these products, it is desired that the fiber length be about 15 mm or less so that the fibers will not have a tendency to "rope" when they are flushed through a toilet. Although fibers of various lengths are applicable in the present invention, desirably fibers are of a length less than about 15 mm so that the fibers disperse easily from one another when in contact with water.

The fabrics of the present invention may be formed from a single layer or multiple layers. In the case of multiple layers, the layers are generally positioned in a juxtaposed or surface-to-surface relationship and all or a portion of the layers may be bound to adjacent layers. Nonwoven webs of the present invention may also be formed from a plurality of separate nonwoven webs wherein the separate nonwoven webs may be formed from single or multiple layers. In those instances where the nonwoven web includes multiple layers, the entire thickness of the nonwoven web may be subjected to a binder application or each individual layer may be separately subjected to a binder application and then combined with other layers in a juxtaposed relationship to form the finished nonwoven web.

In one embodiment, the fabric substrates of the present invention may be incorporated into cleansing and body fluid absorbent products such as sanitary napkins, diapers, surgical dressings, tissues, wet wipes, and the like. These products may include an absorbent core, comprising one or more layers of an absorbent fibrous material. The core may also comprise one or more layers of a fluid-pervious element, such as fibrous tissue, gauze, plastic netting, etc. These are generally useful as wrapping materials to hold the components of the core together. Additionally, the core may comprise a fluid-impervious element or barrier means to preclude the passage of fluid through the core and on the outer surfaces of the product. Preferably, the barrier means also is water-dispersible. A film of a polymer having substantially the same composition as the aforesaid water-dispersible binder is particularly well-suited for this purpose. In accordance with the present invention, the polymer compositions are useful for forming each of the above-mentioned product components including the layers of absorbent core, the fluid-pervious element, the wrapping materials, and the fluid-impervious element or barrier means.

The binder formulations are particularly useful for binding fibers of air-laid nonwoven fabrics. These air-laid materials are useful for body-side liners, fluid distribution materials, fluid in-take materials, such as a surge material, absorbent wrap sheet and cover stock for various water-dispersible personal care products. Air-laid materials are particularly useful for use as a premoistened wipe. The basis weights for air-laid non-woven fabrics may range from about 20 to about 200 grams per square meter (gsm) with staple fibers having a 2–3 denier and a length of about 6–15 millimeters. Surge or in-take materials need better resiliency and higher loft so staple fibers having about 6 denier or greater are used to make these products. A desirable final density for the surge or in-take materials is between about 0.025 grams per cubic centimeter (g/cc) to about 0.050 g/cc. Fluid distribution materials may have a higher density, in the desired range of about 0.10 to about 0.20 g/cc using fibers of lower denier, most desirable fibers have a denier of less than about 1.5. Wipes generally, have a density of about 0.05 g/cc to about 0.2 g/cc and a basis weight of about 30 gsm to about 90 gsm.

One particularly interesting embodiment of the present invention is the production of premoistened wipes, or wet wipes, from the above-described ion-sensitive polymers and fibrous materials. For wipes, the nonwoven fabric is, desirably, formed from relatively short fibers, such as wood pulp fibers. The minimum length of the fibers depends on the method selected for forming the nonwoven fabric. Where the nonwoven fabric is formed by the wet or dry method, the fiber length is desirably from about 0.1 millimeters to 15 millimeters. Desirably, the nonwoven fabric of the present invention has a relatively low wet cohesive strength when it is not bonded together by an adhesive or binder material. When such nonwoven fabrics are bonded together by an adhesive, which loses its bonding strength in tap water and in sewer water, the fabric will break up readily by the agitation provided by flushing and moving through the sewer pipes.

The finished wipes may be individually packaged, preferably in a folded condition, in a moisture proof envelope or packaged in containers holding any desired number of sheets in a water-tight package with a wetting agent applied to the wipe. Relative to the weight of the dry fabric, the wipe may contain from about 10 percent to about 400 percent and desirably from about 100 percent to about 300 percent of the wetting agent. The wipe must maintain its desired characteristics over the time periods involved in warehousing, transportation, retail display and storage by the consumer. Accordingly, shelf life may range from two months to two years.

Various forms of impermeable envelopes for containing wet-packaged materials such as wipes and towelettes and the like are well known in the art. Any of these may be employed in packaging the premoistened wipes of the present invention.

In one embodiment of the present invention, wet wipes, comprising the above-described nonwoven fabric, are stored in an impermeable package and saturated with a salt solution containing greater than about 0.5 weight percent of one or more monovalent salts, such as NaCl or KCl. Desirably, the salt solution contains about 0.5 to 3.0 weight percent of one or more monovalent salts. In another embodiment, the wet wipes are saturated with a salt solution containing greater than about 500 ppm of one or more multivalent ions, such as $Ca^{2+}$ or $Mg^{2+}$ ions. In a further embodiment, the wet wipes are saturated with a salt solution containing greater than about 0.5 weight percent of one or more monovalent salts in combination with one or more multivalent ions, wherein the concentration of multivalent ions is greater than about 500 ppm. Desirably, the wet wipes possess an in-use tensile strength of at least 100 g/in, and a tensile strength of less than about 30 g/in after being soaked in water having a concentration of $Ca^{2+}$ and/or $Mg^{2+}$ ions of about 50 ppm for about one hour. More desirably, the wet wipes possess an in-use tensile strength of at least 300 g/in, and a tensile strength of less than about 30 g/in after being soaked in water having a concentration of $Ca^{2+}$ and/or $Mg^{2+}$ ions of about 50 ppm for about one hour. In a further embodiment, the wet wipes desirably possess an in-use tensile strength of at least 200 g/in, and a tensile strength of less than about 20 g/in after being soaked in water having a concentration of $Ca^{2+}$ and/or $Mg^{2+}$ ions of about 200 ppm for about one hour. Even more desirably, the wet wipes possess an in-use tensile strength of at least 300 g/in, and a tensile strength of less than about 20 g/in after being soaked in water having a concentration of $Ca^{2+}$ and/or Mg 2+ ions of about 200 ppm for about one hour.

The nonwoven fabrics of the present invention may also be incorporated into such body fluid absorbing products as sanitary napkins, diapers, surgical dressings, tissues and the like. The binder is such that it will not dissolve when contacted by body fluids since the concentration of ions in the body fluids is above the level needed for dissolution. The nonwoven fabric retains its structure, softness and exhibits a toughness satisfactory for practical use. However, when brought into contact with water having a concentration of multivalent ions, such as $Ca^{2+}$ and $Mg^{2+}$ ions, of up to about 200 ppm, the binder disperses. The nonwoven fabric structure is then easily broken and dispersed in the water.

In one embodiment of the present invention, the in-use tensile strength of a nonwoven fabric is enhanced by forming the nonwoven fabric with a binder material comprising an ion sensitive polymer of the present invention and subsequently applying one or more monovalent and/or multivalent salts to the nonwoven fabric. The salt may be applied to the nonwoven fabric by any method known to those of ordinary skill in the art including, but not limited to, applying a solid powder onto the fabric and spraying a salt solution onto the fabric. The amount of salt may vary depending on a particular application. However, the amount of salt applied to the fabric is typically from about 0.1 wt % to about 10 wt % salt solids based on the total weight of the fabric. The salt-containing fabrics of the present invention may be used in a variety of fabric applications including, but not limited to, feminine pads and diapers.

Those skilled in the art will readily understand that the binder formulations and fibrous substrates of the present invention may be advantageously employed in the preparation of a wide variety of products, including but not limited to, absorbent personal care products designed to be contacted with body fluids. Such products may only comprise a single layer of the fibrous substrate or may comprise a combination of elements as described above. Although the binder formulations and fibrous substrates of the present invention are particularly suited for personal care products, the binder formulations and fibrous substrates may be advantageously employed in a wide variety of consumer products.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Preparation of Ion-sensitive Polymers

Acrylic acid (43.3 g, 0.60 mol), AMPS (10.7 g, 0.052 mol), butyl acrylate (35.2 g, 0.27 mol), and 2-ethylhexyl acrylate (20 g, 0.11 mol) were dissolved in 55 g of acetone/water (70/30) mixture. An initiator, 2,2-azobisisobutyronitrile (AIBN) (0.51 g, 3.1×10$^{-3}$ mol), was dissolved in 20 ml of acetone. The monomer solution was deoxygenated by bubbling N$_2$ through the solution for 20 minutes. To a 1000 ml three-neck round bottom flask, equipped with a condenser, two addition funnels and a magnetic stirrer, was added 120 g of an acetone/water (70/30) mixture. The solvent was heated to gentle reflux under nitrogen. Monomers and initiator were added simultaneously from the addition funnels over a period of two hours. Polymerization was allowed to proceed for an additional two hours, at the end of which, the addition funnels and condenser were replaced with a distillation head and a mechanical stir rod to remove acetone. A steady stream of N$_2$ was kept during distillation while the temperature was increased gradually from about 65° C. to about 90° C. When the distillation was completed, 400 g of deionized water was added to reduce the viscosity of the polymer solution. A hazy, but uniform solution was obtained.

A total of twelve polymers (Samples 1–12) were synthesized using the above-described procedure. NaOH (2.1 g, 0.052 mol) in 20 ml of water was added at room temperature to neutralize the AMPS component in Samples 3–7 and 9–12. The compositions of Samples 1–12 are summarized in Table 1 below. All percentages are given in mole percent.

TABLE 1

Ion-Sensitive Polymer Compositions

| Sample | % AMPS | % NaAMPS | % AA | % BA | % EHA |
|---|---|---|---|---|---|
| 1 | 1.5 | 0.0 | 65.5 | 22.5 | 10.5 |
| 2 | 3.0 | 0.0 | 64.0 | 22.5 | 10.5 |
| 3 | 0.0 | 3.0 | 64.0 | 22.5 | 10.5 |
| 4 | 0.0 | 3.5 | 63.5 | 22.5 | 10.5 |
| 5 | 0.0 | 3.9 | 62.1 | 24.6 | 9.4 |
| 6 | 0.0 | 4.0 | 57.0 | 26.5 | 12.5 |
| 7 | 0.0 | 4.2 | 64.7 | 19.7 | 11.4 |
| 8 | 5.0 | 0.0 | 62.0 | 22.5 | 10.5 |
| 9 | 0.0 | 5.0 | 58.0 | 26.5 | 10.5 |
| 10 | 0.0 | 4.0 | 63.0 | 21.5 | 11.5 |
| 11 | 0.0 | 5.0 | 59.0 | 25.5 | 10.5 |
| 12 | 0.0 | 5.0 | 60.0 | 24.5 | 10.5 |

COMPARATIVE EXAMPLE 1

Comparative Testing of a Polymer Supplied from Lion Corporation

A Lion polymer was supplied from Lion corporation and tested as outlined in the examples below. The polymer was one of the polymers disclosed and claimed in U.S. Pat. No. 5,312,883, assigned to Lion Corporation.

COMPARATIVE EXAMPLE 2

Preparation of a Lion Corporation Polymer

A Lion polymer was produced using the polymerization procedure outlined in Example 2 of U.S. Pat. No. 5,312,883. The following monomers were used: acrylic acid (50 g, 69 mol), butyl acrylate (25 g, 0.20 mol), and 2-ethylhexyl acrylate (25 g, 0.14 mol). The polymer was neutralized with 0.1 mol sodium hydroxide.

EXAMPLE 2

Improved Hard Water Sensitivity of Unneutralized Polymer Compared to the Lion Polymers The sensitivity of the unneutralized polymers of Example 1 and the Lion polymers of Comparative Examples 1 and 2 to divalent cations present in hard water was measured. Samples 1, 2, and 8 of Example 1 and the Lion polymer were placed in a number of CaCl$_2$ solutions with a Ca$^{2+}$ concentration varying from 100 to 1000 ppm. Following soaking for an hour, the solubility of each polymer was noted. The solubility results are given below in Table 2.

TABLE 2

Solubility Results

| | Solubility in Ca$^{2+}$ | | | |
|---|---|---|---|---|
| Sample | 100 ppm | 200 ppm | 300 ppm | 1000 ppm |
| Sample 1 | 1 | 2 | 3 | 5 |
| Sample 2 | 1 | 2 | 2 | 5 |
| Sample 8 | 1 | 1 | 1 | 5 |
| Comp. Ex. 1 | 4 | 5 | 5 | 5 |
| Comp. Ex. 2 | 2 | 4 | 4 | 5 |

Note:
1: very light cloudiness;
2: light cloudiness;
3: moderate cloudiness (cloudy, but light still able to penetrate through solution);
4: severe cloudiness (milky);
5: heavy precipitation (solid gel formation).

The results of Table 2 indicate that the AMPS-containing polymers were much less sensitive to Ca$^{2+}$ ion concentration relative to the Lion polymers. However, with a sufficient amount of Ca$^{2+}$ ion present (about 1000 ppm), all of the polymers will "salt out" of the solution. In other words, all of the polymers will be insoluble in the 1000 ppm Ca$^{2+}$ ion solution.

A further dissolution experiment supported these results. The five precipitates were then removed from the 1000 ppm Ca$^{2+}$ solutions and placed in deionized water. Samples 1, 2 and 8, which contained AMPS, redissolved in the deionized water; however, the Lion polymers (from Comparative Examples 1–2) did not due to irreversible crosslinking of the sodium acrylate sites.

Reduction in the ion sensitivity of AMPS-containing polymers toward multivalent ions was found to be not limited to Ca$^{2+}$ ions. In a separate experiment, Samples 2 and 8 along with the Lion polymers of Comparative Examples 1–2 were precipitated in a ZnCl$_2$ solution having a Zn$^{2+}$ ion concentration of 5000 ppm. The precipitates of Sample 2 and 8 redissolved in water, but the Lion polymers did not. This suggested that, in general, the AMPS-containing polymers were less sensitive toward divalent cations and did not form a permanent cross-linking structure.

EXAMPLE 3

Testing the Binding Strength of the AMPS-Containing Polymers Compared to the Lion Polymer The binding strength of the AMPS-containing polymers was tested in 100 and 200 ppm Ca$^{2+}$ solutions. The five polymers (Samples 1, 2 and 8 and the Lion polymers of Comparative Examples 1 and 2) were applied via a #20 wire-wound rod to five identical water-dispersible, wet-laid non-woven webs composed of BFF rayon fibers (1.5 d×25 mm). The fabric samples were dried in a forced-air oven at 50° C. The add-on level was between about 55 and 61 wt % based on the total weight of the fabric. The non-woven sheets were cut to provide 1 inch×3 inch strips from each sheet. The dry samples were put directly into $Ca^{2+}$ ion solutions. The strips were tested for tensile strength after soaking in solution for an hour according to the following test method.

The strips were mounted onto a minitensile tester with a 2" grip separation. The strength was tested at a speed of 18 cm/min and the maximum peak load was recorded. The results are summarized in Table 3 below.

TABLE 3

Tensile Strength

| Sample | Strength (g/in) in $Ca^{2+}$ (ppm) Solutions | |
|---|---|---|
| | 100 ppm | 200 ppm |
| Sample 1 | 0 | 360 |
| Sample 2 | 0 | 361 |
| Sample 8 | 0 | 0 |
| Comp. Ex. 1 | 292 | 529 |
| Comp. Ex. 2 | 281 | 567 |

The results of Table 3 again illustrate the reduced sensitivity of AMPS-containing polymers toward $Ca^{2+}$ ions. Binders composed of Sample 1 and 2 were dispersible in 100 ppm. $Ca^{2+}$ solutions and a binder composed of Sample 8 was dispersible in solution containing up to 200 ppm $Ca^{2+}$. These polymers showed a significant improvement over the Lion polymers.

EXAMPLE 4

Adjusting the pH of Solutions Containing the Ion-sensitive Polymers

The solution pH of Samples 1, 2 and 8 of Example 1 were found to be quite low, ranging from 1.7 for Sample 8 to 2.1 for Sample 1, due to the presence of sulfonic acid groups. Low pH is undesirable in applications such as wet wipes, not only because it causes yellowing of the pulp substrate in the drying process, but it may irritate the skin during use. To adjust the pH of these solutions, equimolar amounts of NaOH were added to neutralize the AMPS. The pH of the solutions rose to about 3.1–3.3, a more desirable pH range for skin health, which also eliminates yellowing of the fibrous substrate during drying.

EXAMPLE 5

Effect of Neutralization on the Dispersion Rate of Ion-sensitive Polymers

Five polymer solutions containing three polymers of Example 1 (Samples 1–3) and the Lion polymers of Comparative Examples 1–2 were applied via a #20 wire-wound rod to five identical water-dispersible, wet-laid non-woven webs composed of BFF rayon fibers (1.5 d×25 mm). The fabric samples were dried in a forced-air oven at 50° C. The add-on level was between about 55 and 61 wt % based on the total weight of the fabric. The non-woven sheets were cut to provide 1 inch×3 inch strips from each sheet.

The strips were placed in deionized water. The time of dispersion (i.e., the time at which each fabric sample had substantially zero tensile strength) was recorded. Results are given in Table 4 below.

TABLE 4

Time of Dispersion in Deionized Water

| Fabric Sample | Time to Disperse |
|---|---|
| 1 | >2 hours |
| 2 | >2 hours |
| 3 | ~10 minutes |
| Comp. Ex. 1 | ~3 minutes |
| Comp. Ex. 2 | ~3 minutes |

As shown in Table 4, the strips containing Lion polymer lost all of their strength in about three minutes, indicating good dispersibility in deionized water. The strips formed from the AMPS-containing polymers had poor dispersibility in deionized water. However, the strips formed from the NaAMPS-containing polymer had good dispersibility in deionized water.

In order to determine the effect of $Ca^{2+}$ ion concentration on the dispersibility of Sample 3, strips of Sample 3 were tested for tensile strength after soaking for up to one hour in solutions containing from 0 to 200 ppm $Ca^{2+}$ ion. The sample was found to be stable in a 0.9 wt % NaCl solution, and dispersable in deionized water in less than 10 minutes. In a 200 ppm $Ca^{2+}$ solution, the strip had an initial strength of about 275 g/in. In a 100 ppm $Ca^{2+}$ solution, the strip had the strength of less than about 50 g/in after one hour and became unrecognizable after two hours. It was concluded that while neutralization increased the dispersion rate significantly, it did not negatively alter the strength characteristics and $Ca^{2+}$ sensitivity of the ion-sensitive polymers of the present invention.

EXAMPLE 6

Water-Dispersibility Testing of Nonwoven Fabrics

Ten polymer solutions containing eight polymers of Example 1 (Samples 1 and 3–9) and the Lion polymers of Comparative Examples 1–2 were applied via a #20 wire-wound rod to ten identical water-dispersible, wet-laid non-woven webs composed of BFF rayon fibers (1.5 d×25 mm). The fabric samples were dried in a forced-air oven at 50° C. The add-on level was between about 55 and 61 wt % based on the total weight of the fabric. The non-woven sheets were cut to provide 1 inch×3 inch strips from each sheet. The strips were tested for water-dispersibility according to the following procedure.

The 1 inch×3 inch strips from the ten nonwoven sheets were soaked in solutions having a $Ca^{2+}$ ion concentration from 100 to 1000 ppm for about one hour. The samples were removed from the solutions and tested for tensile strength in the machine direction using the procedure outlined above. Samples having a low tensile strength showed good water-dispersibility. Test results are given below in Table 5.

TABLE 5

| Tensile Strength of Ion-Sensitive Polymers in $Ca^{2+}$ Ion Solutions (ppm $Ca^{2+}$ Ion) (g/in) | | | | |
|---|---|---|---|---|
| Fabric Sample | 100 ppm | 200 ppm | 500 ppm | 1000 ppm |
| 1 | 0 | 360 | | |
| 3 | 0 | 275 | 498 | |
| 4 | 0 | 39 | 471 | 445 |

TABLE 5-continued

Tensile Strength of Ion-Sensitive Polymers in $Ca^{2+}$ Ion Solutions (ppm $Ca^{2+}$ Ion) (g/in)

| Fabric Sample | 100 ppm | 200 ppm | 500 ppm | 1000 ppm |
|---|---|---|---|---|
| 5 | 0 | 327 | 522 | 441 |
| 6 | 310 | 482 | 529 | |
| 7 | 0 | 0 | 301 | 335 |
| 8 | 0 | 0 | | |
| 9 | 0 | 21 | 510 | 503 |
| Comp. Ex. 1 | 292 | 529 | | |
| Comp. Ex. 2 | 281 | 567 | 813 | 799 |

As shown in Table 5, the tensile strength of the nonwoven fabrics formed from the AMPS-containing or NaAMPS-containing polymers, in most cases, decreased as the concentration of $Ca^{2+}$ ion decreased. By controlling the hydrophobic/hydrophilic balance in the composition of the polymeric binder, nonwoven fabrics were produced having good water-dispersibility as identified by a low tensile strength in solutions having a $Ca^{2+}$ ion concentration of 100 or 200 ppm (see Samples of Polymer 4, 7, 8, and 9 above).

In contrast, the water-dispersibility or ion-triggerability of the Lion polymers was found to be unacceptable for flushable applications. The nonwoven fabrics formed from the Lion polymers had an extremely high tensile strength (>281 g/in) in solutions having a $Ca^{2+}$ ion concentration of 100 or 200 ppm. Given these results, nonwoven fabrics formed from the Lion polymers would not be suitable in flushable products in areas of hard water.

EXAMPLE 7

Variation of the Composition of NaAMPS-Containing Polymers to Affect Tensile Strength in NaCl Solutions and Dispersibility in $Ca^{2+}$ Solutions Ten nonwoven fabrics comprising binder materials formed from eight polymers of Example 1 (Samples 4–7 and 9–12) and the Lion polymers of Comparative Examples 1–2 were prepared as in Example 7. In-use strength and dispersibility of the NaAMPS-containing fabrics and the Lion polymer-containing fabrics were measured as described above.

The 1 inch×3 inch strips from the ten nonwoven sheets were tested on a machine using the test method described above. In-use strength of the polymeric binder was measured as the tensile strength in the machine direction of each sample tested in a 0.9 wt % NaCl salt solution or a 1.5 wt % NaCl salt solution after soaking overnight at room temperature, unless otherwise indicated.

To determine the dispersibility of some of the pre-soaked samples, the sample was transferred after soaking in one of the above salt solutions to a solution containing a $Ca^{2+}$ ion concentration from 100 to 200 ppm $Ca^{2+}$ for an hour, and tested for tensile strength. Samples having a low tensile strength showed good water-dispersibility. Test results are given below in Table 6.

TABLE 6

Tensile Strength of Ion-Sensitive Polymers in $Ca^{2+}$ Ion Solutions (ppm $Ca^{2+}$ Ion) and NaCl Solutions (g/in)

| Fabric Sample | 0.9 wt % NaCl | 1.5 wt % NaCl | 100 ppm $Ca^{2+}$ | 150 ppm $Ca^{2+}$ | 200 ppm $Ca^{2+}$ |
|---|---|---|---|---|---|
| 4* | 0 | 364 | 0 | | 39 |
| 5* | 0 | 350 | 0 | | 327 |
| 6* | 315 | | 310 | | 482 |
| 7* | 0 | 322 | 0 | | 0 |
| 9** | 0 | 449 | | | 62 |
| 10** | 0 | 378 | | 52 | 155 |
| 11** | | 442 | | | 0 |
| 12** | | 386 | | | 0 |
| Comp. Ex. 1* | 529 | | 292 | | 529 |
| Comp. Ex. 2** | 375 | 645 | 699 | | 698 |

Note:
*Samples were tested after 1 hour soaking in the designated solution.
**Dry samples were pre-soaked overnight in a NaCl solution, then put directly into a $Ca^{2+}$ solution, and tested after 1 hour.

As shown in Table 6, the fabric samples formed from NaAMPS-containing polymers had very little tensile strength in 0.9 wt % NaCl solution. In contrast, fabric samples formed from the Lion polymers had high tensile strength. In the 1.5 wt % NaCl solution, fabric samples formed from NaAMPS-containing polymers had good tensile strength. The increase in tensile strength may be attributed to an increase in the salting-out effect of the NaAMPS-containing polymers.

Further, Table 6 shows that most of the fabric samples formed from NaAMPS-containing polymers lost all or a significant portion of their tensile strength after soaking in a 100 ppm $Ca^{2+}$ ion solution. Also, fabric samples 11 and 12 lost their tensile strength after being transferred to and soaking in a 200 ppm $Ca^{2+}$ ion solution, indicating good water dispersibility. In contrast, fabric samples formed from the Lion polymers did not lose their tensile strength in 100 ppm or 200 ppm $Ca^{2+}$ ion solutions, indicating poor dispersibility.

EXAMPLE 8

Effect of Divalent Ion Salts on the In-Use Tensile Strength and Water-Dispersibility of Nonwoven Fabrics Bound with NaAMPS-Containing Polymers Example 7 indicates that NaAMPS-containing polymers, that are dispersible in 200 ppm $Ca^{2+}$ solution, have acceptable in-use tensile strength only in higher NaCl concentrations (greater than 0.9 wt % NaCl). In order to possibly increase the tensile strength of these binders at a lower NaCl concentration, salts containing divalent cations such as $Ca^{2+}$ and $Zn^{2+}$ were added to the NaCl solutions because of their higher salting-out capability. Samples 3–7 and 9 of Example 1 were used as binder material for nonwoven fabrics comprising BFF rayon fibers as described above. Tensile strength of the fabrics was measured after soaking in a variety of solutions. Results of the testing are summarized in Table 7 below.

TABLE 7

Tensile Strength of Ion-Sensitive Polymers in Mixed Salts Solutions (g/in)

| Fabric Sample | 500 ppm $Ca^{2+}$ | 1000 ppm $Ca^{2+}$ | 0.9% NaCl with 500 ppm $Ca^{2+}$ | 0.9% NaCl with 1000 ppm $Ca^{2+}$ | 0.9% NaCl with 500 ppm $Zn^{2+}$ |
|---|---|---|---|---|---|
| 3 | 498 |  | 498 |  |  |
| 4 | 471 | 445 |  | 420 | 335 |
| 5 | 522 | 441 |  | 432 |  |
| 6 | 529 |  | 573 |  |  |
| 7 | 301 | 335 | 379 | 335 | 304 |
| 9 | 0 | 503 | 585 | 461 | 379 |

The results of Table 7 indicate that the NaAMPS-containing polymers are stable in all test solutions, demonstrating the effectiveness of divalent ions in stabilizing the polymer, even at low NaCl concentrations. In some cases, the polymers may be stabilized with the divalent ion salt alone. As further shown in Table 7 in comparison with Table 6, $Ca^{2+}$ ions are more effective at stabilizing the polymers than $Na^+$ ions or $Zn^{2+}$ ions, as demonstrated by the higher tensile strength values in the NaCl solutions containing $Ca^{2+}$ ions as opposed to the NaCl solutions containing $Zn^{2+}$ ions in the comparable concentration level.

EXAMPLE 9

Solubility of Ion-Triggerable Polymers as Measured by Percentage Weight Loss in a Divalent Ion Salt Solution Films were produced from three polymers of Example 1 (Samples 9, 10, and 12) and the Lion polymer of Comparative Example 1. Weighed samples of each film were placed in a 1.5 wt % NaCl solution for 24 hours. The samples were removed and weighed to determine the percent weight loss of each sample. Similarly, weighed samples of each film were placed in a solution containing 200 ppm $Ca^{2+}/Mg^{2+}$ ions (2 parts $Ca^{2+}$ to 1 part $Mg^{2+}$) and agitated by shaking for about 2 hours. The samples were removed and weighed to determine the percent weight loss of each sample.

TABLE 8

Percent Weight Loss of Films of Ion-Sensitive Polymers in Salts Solutions

| Sample | % Wt. Loss in 1.5% NaCl | % Wt. Loss in 200 ppm $Ca^{2+}/Mg^{2+}$ |
|---|---|---|
| 9 | 0 | 38 |
| 10 | 0 | 34 |
| 12 | 0 | 100 |
| Comp. Ex. 1 | 0 | 5 |

All five samples show 0% weight loss after being soaked in 1.5% NaCl for 24 hours, indicating that all samples were substantially insoluble in the NaCl solution. In the $Ca^{2+}/Mg^{2+}$ solution, the Lion polymer had very little weight loss, indicating that the Lion polymer was substantially insoluble in the solution. However, the polymers of the present invention had a weight loss of at least 34% in the $Ca^{2+}/Mg^{2+}$ solution, indicating that the samples formed from the ion-triggerable polymers of the present invention were soluble in the solution. Moreover, Sample 12 had a weight loss of 100%, indicating substantial solubility in the $Ca^{2+}/Mg^{2+}$ solution.

The results of Table 8 further confirm the results of Example 6. In particular, the water-dispersibility or ion-triggerability of the Lion polymer was found to be unacceptable for flushable applications, especially flushable applications in areas of hard water. However, the water-dispersibility or ion-triggerability of the polymers of the present invention was found to be acceptable for flushable applications, including flushable applications in areas of hard water.

The above disclosed examples are preferred embodiments and are not intended to limit the scope of the present invention in any way. Various modifications and other embodiments and uses of the disclosed water-dispersible polymers, apparent to those of ordinary skill in the art, are also considered to be within the scope of the present invention.

What is claimed is:

1. An ion-sensitive polymer, wherein the polymer is formed from: acrylic acid; AMPS or NaAMPS; butyl acrylate; and 2-ethylhexyl acrylate; further wherein the polymer is insoluble in a neutral salt solution containing at least about 0.3 weight percent salt, said salt comprising one or more monovalent or multivalent ions; and wherein the polymer is soluble in tap water containing one or more multivalent ions.

2. The ion-sensitive polymer of claim 1, wherein the polymer is insoluble in a neutral salt solution containing at least about 0.3 weight percent salt, said salt comprising one or more monovalent or multivalent ions; and wherein the polymer is soluble in tap water containing from about 15 ppm to about 200 ppm of one or more multivalent ions.

3. The ion-sensitive polymer of claim 2, wherein the polymer is insoluble in a neutral salt solution containing at least about 0.3 weight percent salt, said salt comprising one or more monovalent or multivalent ions; and wherein the polymer is soluble in tap water containing from about 15 ppm to about 150 ppm of one or more multivalent ions.

4. The ion-sensitive polymer of claim 3, wherein the polymer is insoluble in a neutral salt solution containing at least about 0.3 weight percent salt, said salt comprising one or more monovalent or multivalent ions; and wherein the polymer is soluble in tap water containing from about 15 ppm to about 100 ppm of one or more multivalent ions.

5. The ion-sensitive polymer of claim 4, wherein the polymer is insoluble in a neutral salt solution containing at least about 0.3 weight percent salt, said salt comprising one or more monovalent or multivalent ions; and wherein the polymer is soluble in tap water containing from about 15 ppm to about 50 ppm of one or more multivalent ions.

6. The ion-sensitive polymer of claim 1, wherein the polymer is insoluble in a neutral salt solution containing from about 0.5 weight percent to about 5.0 weight percent of the salt.

7. The ion-sensitive polymer of claim 1, wherein the polymer is insoluble in a neutral salt solution containing from about 0.5 weight percent to about 3.0 weight percent of the salt.

8. The ion-sensitive polymer of claim 1, wherein the multivalent ions comprise $Ca^{2+}$ ions, $Mg^{2+}$ ions, $Zn^{2+}$ ions, or a combination thereof.

9. The ion-sensitive polymer of claim 1, wherein the monovalent ions comprise $Na^+$ ions, $Li^+$ ions, $K^+$ ions, $NH_4^+$ ions, or a combination thereof.

10. The ion-sensitive polymer of claim 1, wherein the polymer is formed from one or more monomers selected from styrenesulfonic acid (SS), sodium salt of styrenesulfonic acid (NaSS), 2-acrylamido-2-methyl-1-propanesulfonic acid (AMPS), sodium salt of 2-acrylamido-2-methyl-1-propanesulfonic acid (NaAMPS), vinylsulfonic acid, sodium salt of vinylsulfonic acid, or combinations thereof.

11. The ion-sensitive polymer of claim 1, wherein the polymer comprises from about 50 to less than 67 mol % acrylic acid; from greater than 0 to about 10 mol % AMPS or NaAMPS; from about 15 to about 28 mol % butyl acrylate; and from about 7 to about 15 mol % 2-ethylhexyl acrylate.

12. The ion-sensitive polymer of claim 11, wherein the polymer comprises from about 57 to less than 6 mol % acrylic acid; from about 1 to about 6 mol % AMPS or NaAMPS; from about 15 to about 28 mol % butyl acrylate; and from about 7 to about 13 mol % 2-ethylhexyl acrylate.

13. A binder composition for binding fibrous material into an integral web, said binder composition comprising the ion-sensitive polymer of claim 1.

14. An ion-sensitive polymer formed from four monomers: acrylic acid, AMPS or NaAMPS, butyl acrylate, and 2-ethylhexyl acrylate; wherein the polymer is insoluble in a neutral salt solution containing at least about 0.3 weight percent salt, said salt comprising one or more monovalent or multivalent ions; and wherein the polymer is soluble in tap water containing from about 15 ppm to about 500 ppm of one or more multivalent ions.

15. The ion-sensitive polymer of claim 14, wherein the polymer comprises from about 50 to less than 67 mol % acrylic acid; from greater than 0 to about 10 mol % AMPS or NaAMPS; from about 15 to about 28 mol % butyl acrylate; and from about 7 to about 15 mol % 2-ethylhexyl acrylate.

16. The ion-sensitive polymer of claim 15, wherein the polymer comprises from about 57 to less than 66 mol % acrylic acid; from about 1 to about 6 mol % AMPS or NaAMPS; from about 15 to about 28 mol % butyl acrylate; and from about 7 to about 13 mol % 2-ethylhexyl acrylate.

17. A binder composition for binding fibrous material into an integral web, said binder composition comprising the ion-sensitive polymer of claim 14.

* * * * *